United States Patent [19]

Woolard

[11] Patent Number: 4,960,457
[45] Date of Patent: Oct. 2, 1990

[54] SUBSTITUTED 1,3-DIPHENYL PYRROLIDONES AND THEIR USE AS HERBICIDES

[75] Inventor: Frank X. Woolard, Richmond, Calif.

[73] Assignee: ICI Americas Inc., Wilmington, Del.

[21] Appl. No.: 290,080

[22] Filed: Dec. 27, 1988

[51] Int. Cl.$^5$ .................. C07D 207/26; A01N 43/36
[52] U.S. Cl. ............................. 71/95; 548/543; 548/550
[58] Field of Search ............... 548/543, 550; 71/95

[56] References Cited

U.S. PATENT DOCUMENTS

| | | | |
|---|---|---|---|
| 4,012,495 | 3/1977 | Schmiechen | 548/543 |
| 4,110,105 | 8/1978 | Teach | 71/95 |
| 4,210,589 | 7/1980 | Teach | 260/326.5 FL |
| 4,296,029 | 10/1981 | Bushell et al. | 548/543 |
| 4,439,229 | 3/1984 | Swithenbank | 548/549 |
| 4,645,843 | 2/1987 | Broadhurst et al. | 548/543 |

Primary Examiner—David B. Springer
Attorney, Agent, or Firm—Michael J. Bradley

[57] ABSTRACT

Substituted 1,3-diphenyl pyrrolidones of the formula

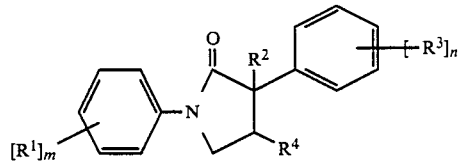

in which $R^1$ and $R^3$ are halogen, trifluoromethyl, cyano, alkyl or alkoxy, $R^2$ is H or halogen, and $R^4$ is alkyl or haloalkyl, are useful as herbicidal agents.

78 Claims, No Drawings

SUBSTITUTED 1,3-DIPHENYL PYRROLIDONES AND THEIR USE AS HERBICIDES

BACKGROUND AND SUMMARY OF THE INVENTION

This invention relates to substituted pyrrolidones and to their use in herbicidal formulations. In particular, this invention relates to substituted 1,3-diphenyl pyrrolidones of the formula

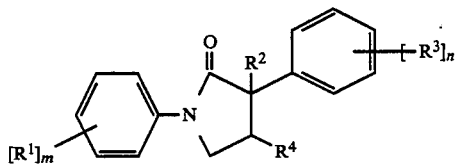

in which:
m is 1, 2, 3, 4 or 5;
n is 0, 1, 2, 3, 4 or 5;
'R' is a member selected from the group consisting of halogen, trifluoromethyl, cyano, $C_1$-$C_4$ alkyl and $C_1$-$C_4$ alkoxy, and, when m is greater than 1 may be either a single such member or a combination thereof:
'$R^2$ is a member selected from the group consisting of H and halogen: $R_3$ is a member selected from the group consisting of
halogen trifluoromethyl, cyano, $C_1$-$C_4$ alkyl and $C_1$-$C_4$ alkoxy, and, when n is greater than 1, may be either a single such member or a combination thereof: and
$R^4$ is a member selected from the group consisting of $C_1$-$C_4$ alkyl and halogen-substituted $C_1$-$C_4$ alkyl.

The compounds of the present invention, as will be seen from the description and test data which follows, have utility as both pre-emergence and post-emergence herbicides, against a wide range of plant species. These compounds are of particular utility in the control of weeds associated with rice crops, notably upland rice. Preferred methods of application to rice crops are post-emergence pre-flood application and pre-emergence spray application.

The terms "herbicide" and "herbicidal" are used herein to denote the inhibitive control or modification of undesired plant growth. Inhibitive control and modification include all deviations from natural development such as, for example, total killing, growth retardation, defoliation, desiccation, regulation, stunting, tillering, stimulation, leaf burn, and dwarfing. The term "herbicidally effective amount" is used to denote any amount which achieves such control or modification when applied to the undesired plants themselves or to the area in which these plants are growing. The term "plants" is intended to include germinant seeds, emerging seedlings and established vegetation, including both roots and above-ground portions.

DETAILED DESCRIPTION OF THE INVENTION AND PREFERRED EMBODIMENTS

Within the scope of the above formula, certain embodiments are preferred, as follows.

$R^1$ is preferably halogen, trifluoromethyl or cyano. Of these, halogen and trifluoromethyl are particularly preferred, notably chloro, fluoro and trifluoromethyl.

Note that where more than one $R^1$ are present (i.e.. when m is 2 or greater). the $R^1$'s may be the same or different. Preferred positions for $R^1$ on the phenyl ring from which it depends are the meta- and para-positions, with the metaposition particularly preferred.

'$R^2$ is preferably H $R^3$ is preferably halogen. $C_1$ to $C_4$ alkyl, or $C_1$ to $C_4$ alkoxy. Of the halogens, chloro and bromo are preferred. and of the alkyls and alkoxy's methyl and methoxy are preferred, respectively. The preferred position for $R^3$ on the phenyl ring from which it depends is the meta-position. As in the case of $R^1$, where more than one $R^3$ are present (i.e., when n is 2 or greater), the $R^3$'s may be the same or different.

$R^4$ is preferably methyl, ethyl, halomethyl or haloethyl.

Preferred values for m are 1 and 2. with m=1 particularly preferred. Preferred values for n are 0, 1 and 2, with 1 and 2 particularly preferred, and 1 the most preferred.

The terms "alkyl" and "alkoxy" are intended to include both straight-chain and branched-chain groups. The alkyl groups thus include methyl, ethyl, n-propyl, isopropyl, n-butyl, isobutyl, s-butyl and t-butyl, and the alkoxy groups likewise.

The compounds of the present invention may be prepared by a variety of synthesis routes. Some of these routes are as follows.

Those compounds bearing a chloromethyl group at the R. position are prepared by a stepwise sequence of transformations beginning with the reaction of an appropriately substituted benzaldehyde with an appropriately substituted aniline to form an imine:

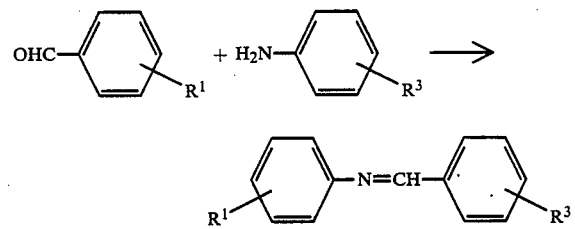

This step is conducted at reflux in a nonpolar, water-immiscible organic solvent such as benzene or toluene, and catalyzed by the presence of a small amount of an aromatic sulfonic acid such as p-toluenesulfonic acid. The formation of the imine is driven to completion by the azeotropic removal of water as it is formed.

The product imine is then dissolved in a nonpolar solvent such as benzene, toluene or methylene chloride at a temperature of 15-30° C. with chloroform and 50% aqueous sodium hydroxide. A phase transfer catalyst such as a tetraalkylammonium salt, notably tetrabutylammonium bromide, is used to facilitate the passage of reactive species across the water-methylene chloride boundary. The dichlorocarbene thus formed reacts with the imine to form a dichloroaziridine of the formula:

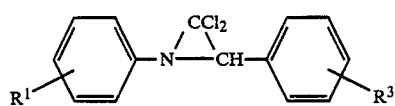

This species is heated neat at 100-105° C. under an inert atmosphere to rearrange to an imidoyl chloride:

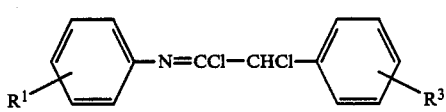

The imidoyl chloride is then dissolved in an aprotic solvent such as methylene chloride or benzene, along with a weak organic base such as pyridine or triethylamine, and converted by the addition of 100 mole % of an allyl alcohol to an O-allylimidate:

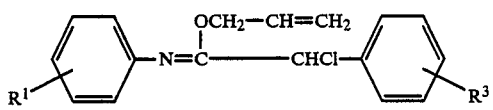

During this process, which liberates heat, the temperature is maintained between 5° C. and 20° C. with external cooling.

The imidate is then rearranged to an N-allyl-α-chlorophenylacetamide:

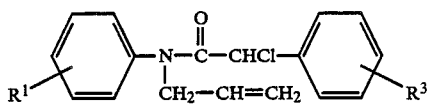

In this process, conducted without solvent at 100-120° C. a zero-valent palladium species such as tetrakis(triphenylphosphine)palladium(O) is used.

The final step of forming the pyrrolidone ring is effected in accordance with the process described in Broadhurst hurst et al., U.S. Pat. No. 4,645,843, Feb. 24, 1987, incorporated herein by reference.

Those compounds bearing an alkyl group at the $R^4$ position are prepared by reacting a substituted N-allylaniline dissolved in an aprotic solvent such as methylene chloride chloroform or benzene with a substituted α-chlorophenyl acetyl chloride. The N-allylaniline is prepared by procedures described in commonly owned U.S. patent application Ser. No. 07/126,134, filed November 27, 1987, incorporated herein by reference. The α-chlorophenyl acetyl chloride is prepared by the process described in Sauter. et al., U.S. Pat. No. 4,297,364 Oct. 27, 1981, incorporated herein by reference. The reaction between the N-allylaniline and the α-chlorophenyl acetyl chloride is as follows:

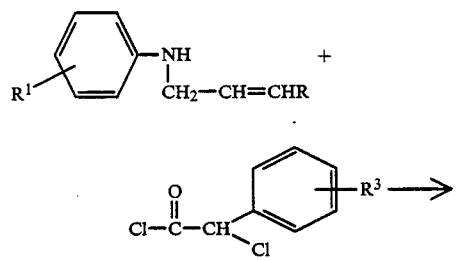

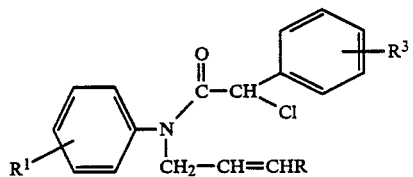

where R denotes H or lower alkyl. The reaction is conducted in the presence of an organic base such as triethylamine or pyridine to neutralize the acid liberated during the course of the reaction. During this process, which liberates heat, the temperature is maintained at 5-20° C. with external cooling.

The resulting anilide is then cyclized to the final pyrrolidone by conventional procedures.

It will be noted that the generic formula representing the substituted 1,3-diphenyl pyrrolidones of the present invention indicates two chiral centers, one at the 3-position and the other at the 4-position of the pyrrolidone ring. The specific compounds disclosed herein each represent a mixture of enantiomers at both chiral centers, unless otherwise indicated. Herbicidal activity for the mixture is an indication of herbicidal activity for each individual enantiomer. In certain cases, however, as is known among those skilled in the art, one enantiomer will have a greater herbicidal activity than the other enantiomer for a given chiral center. In this particular case, when both chiral centers are taken into consideration, those enantiomers having the cis configuration are sterically unfavored and less active.

The following are examples of compounds which have been synthesized by the procedures described above. These examples are offered strictly for purposes of illustration, and are intended neither to limit nor to define the invention in any manner.

EXAMPLE 1

This example illustrates the preparation of 1-(3-trifluoromethyl)phenyl-3-(3-chloro)phenyl-4-chloromethyl-2-pyrrolidone in which, according to the generic formula given above, $R^1$ is 3-$CF_3$, $R^2$ is H, $R^3$ is 3-Cl, and $R^4$ is $CH^2Cl$. This compound is shown in Table I below as Compound No. 11.

The synthesis was begun by preparing N-(3-trifluoromethyl)phenyl-3-chlorobenzaldehydeimine as follows. To a 300-mL boiling flask equipped with a magnetic stirrer. heating mantle, and reflux condenser carrying a Dean-Starke trap was added 16.11 g (0.10 mol) of m-aminobenzotrifluoride, 14.06 g (0.10 mol) of 3-chlorobenzaldehyde, 150 mL of benzene, and 50 mg of p-toluenesulfonic acid. The mixture was stirred and heated to reflux. After four hours the predicted amount of water (1.8 mL) had collected in the trap and the heating was discontinued. When the solution had cooled to room temperature it was washed with 50 mL of saturated potassium carbonate solution, two 100-mL portions of water, and 100 mL of saturated NaCl solution. The organic phases were dried (MgSO4) and the solvent removed in vacuo to give 27.35 g (96%) of the imine as a pale orange oil.

The imine was then converted to 1-(3-trifluoromethyl)-phenyl-2.2-dichloro-3-(3-chloro)phenylaziridine as follows. To a 500-mL three-necked round-bottomed flask equipped with a mechanical stirrer and pressure equalizing addition funnel were added 27.35 g (96.4 mmol) of the imine 17.95 g (150 mmol) of chloroform. 2.73 g (8.5 mmol) of tetrabutyl-ammonium bromide, and 150 mL of methylene chloride. The mixture was rapidly stirred and 51.44 g (640 mmol) of 50% NaOH solution added dropwise over ten minutes. A 5° C. exotherm was noted during the course of the addition. The stirring was continued for an additional 4.5 hours at which time gas chromatography (GC) analysis showed the reaction to be complete. Water (50 mL) was then added to the reaction mixture and the layers that formed were separated. The organic phase was dried (Nahd 2SO$_4$) and the solvent removed in vacuo to give a black oil. This material was triturated with three 75-mL portions of hot hexanes. The hexane portions were combined, filtered through diatomaceous earth, and the solvent removed in vacuo to afford 30.90 g (87%) of the aziridine as an orange oil.

The aziridine was then converted to the imidoyl chloride as follows. The aziridine (29.60 g. 80.7 mmol) was placed in a 100-mL boiling flask equipped with a nitrogen bubbler. The flask was then immersed in an oil bath and the contents heated to 136° C. After 2.5 hours nuclear magnetic resonance (NMR) showed the reaction to be complete. The crude product was allowed to cool to approximately 70° C. and then triturated with three 50-mL portions of hexanes. The hexane fractions were then combined and the solvent removed in vacuo to give 17.85 g (60%) of the imidoyl chloride as a dark orange syrup.

The imidoyl chloride was then converted to O-allylN-(3-trifluoromethyl)phenyl-α-chloro-(3-chlorophenyl)acetamidate as follows. To a 250-mL three-necked round-bottomed flask equipped with a magnetic stirrer and pressure equalizing addition funnel carrying a nitrogen bubbler were added 1.58 g (27.3 mmol) of allyl alcohol. 3.80 mL (2.76 g. 27.3 mmol) of triethylamine, and 50 mL of methylene chloride. The solution was stirred and a solution of 10.00 g (27.3 mmol) of the imidoyl chloride in 50 mL of methylene chloride was added dropwise over 20 minutes. When the addition was complete the stirring was continued for another two hours and then poured into 150 mL of water. The resulting layers were separated and the organic phase dried with MgSO$_4$. The solvent was then removed %% vacuo to give 10.28 g (97%) of the acetamidate as a dark syrup.

Rearrangement to the N-allyl acetamide was done as follows. To a 100-mL boiling flask equipped with a nitrogen bubbler was added 8.66 g (22.3 mmol) of the imidate and 0.25 g of tetrakis(triphenylphosphine)palladium(O). The flask was then immersed in an oil bath maintained at a temperature range of 100-120° C. After two hours the reaction mixture was cooled to room temperature and dissolved in about 15 mL of 1:1 ethyl acetate/hexanes. After passage through a short column of silica gel to remove some tarry material removal of the solvent afforded 8.80 g (102%) of the N-allyl acetamide as a dark syrup.

The final pyrrolidone was then prepared as follows. To a 200-mL three-necked round-bottomed flask equipped with a magnetic stirrer heating mantle, reflux condenser, glass stopper and thermometer were added 7.47 g (19.2 mmol) of the N-allyl acetamide, 50 mL of toluene, 99 mg (1.0 mmol) of cuprous chloride, and 0.68 g (5.3 mmol) of di-n-butylamine. The mixture was stirred and heated to 90-95° C.

After four hours, analysis of the mixture by thin-layer chromatography (TLC) (1:1 ethyl acetate/hexanes) showed the reaction to be complete. The solution was cooled to room temperature and washed with three 40-mL portions of 3% aqueous HCl solution, and two 40-mL portions of saturated NaCl solution. The organic phase was dried (MgSO$_4$) and the toluene removed in vacuo to give a thick dark oil. Chromatography on silica gel with 1:1 ethyl acetate/hexanes provided 3.01 g (45%) of product as a thick orange syrup. The structure of the product was confirmed as that of 1-(3-trifluoromethyl)phenyl-3-(3-chloro)phenyl-4-chloromethyl-2-pyrrolidone by infrared spectroscopy (IR), nuclear magnetic resonance (NMR), and mass spectroscopy (MS).

This example illustrates the preparation of 1-(3-trifluoromethyl)phenyl-3-trifluoromethyl)phenyl-3-(3-chloro)phenyl-4-ethyl-2-pyrrolidone in which, according to the generic formula given above, $R^1$ is 3-CF$_3$, $R^3$ is H, $R^3$ is 3-Cl, and $R^4$ is C$_2$H$_5$. This compound is shown in Table I below as Compound No. 27.

The synthesis was begun by preparing 3-chloromandellic acid as follows. A 300-mL three-necked round-bottomed flask equipped with a magnetic stirrer, thermometer, and pressure equalizing addition funnel was charged with 50.0 g (0.356 mol) of 3-chlorobenzaldehyde, 75 mL of ether, and 24.0 g (0.368 mol) of KCN. The suspension was cooled by immersing the flask in an ice bath, and 37.5 mL of concentrated HCl was then added dropwise with stirring. The addition was conducted at such a rate that the temperature did not rise above 10° C. When the addition was complete the stirring was continued for one hour at 5° C. and then at ambient temperature for 1.5 hours. The reaction mixture was then poured into 250 mL of 6N HCl and heated to reflux. After 18 hours the solution was cooled and neutralized with 170 mL of 50% aqueous NaOH. The mixture was extracted with three 100 mL portions of ether, acidified with 50 mL of concentrated HCl, and the extraction process repeated. The acidic extracts were combined, dried (MgSO$_4$). and the solvent removed in vacuo to afford 58.71 g (88%) of 3-chloromandellic acid as an egg-white solid.

The 3-chloromandellic acid was then converted to α-chloro-(3-chlorophenyl)acetyl chloride as follows. A 250-mL boiling flask equipped with a magnetic stirrer, heating mantle and reflux condenser carrying a nitrogen bubbler was charged with 22.10 g (0.118 mol) of the acid. 30 mL of toluene, 0.25 mL of dimethylformamide, and 22.0 mL (35.9 g, 0.392 mol) of thionyl chloride. The mixture was stirred and heated to 55° C. Gas evolution ceased within three hours. The volatiles were then removed in vacuo to give 27.91 g (106%) of the acetyl chloride as a mobile orange oil.

The acetyl chloride was then converted to N-crotyl-N-(3-trifluoromethyl-phenyl)-%-chloro-(3-chlorophenyl)acetamide as follows. A 500-mL three-necked round-bottomed flask equipped with a magnetic stirrer, thermometer and pressure equalizing addition funnel carrying a nitrogen bubbler was charged with 7.00 g (32.5 mmol) of N-crotyl-m-aminobenzotrifluoride, 2.77 g (35.5 mmol) of pyridine and 100 mL of methylene chloride. The flask was immersed in an external ice bath and the contents cooled to 5° C. with stirring. A solution of the acetyl chloride in 25 mL of methylene chloride was then added dropwise at such a rate that the temperature did not rise above 10° C. When the addition was complete the stirring was continued for an additional 40 minutes after which time analysis by GC showed the reaction to be complete. The solution was washed with two 50-mL portions of 3% aqueous HCl, two 50-mL portions of water, dried (MgSO$_4$), and the solvent removed %n vac%o to give 14.01 g (107%) of crude product as a thick yellow oil.

The latter was then converted to the final pyrrolidone as follows, A 500-mL three-necked round-bottomed flask equipped with a magnetic stirrer, heating mantle, pressure equalizing addition funnel, and reflux condenser carrying a nitrogen bubbler was charged with 13.73 g (34.1 mmol) of the product prepared in the last paragraph, 0.31 g of azo-bisisobutyronitrile, and 100 mL of benzene. The mixture was stirred, heated to reflux and 10.19 g (35.0 mmol) of tri-n-butyltin hydride in 55 mL of benzene added dropwise over 2.5 hours. When the addition was complete the refluxing was continued for an additional four hours and the solvent was then removed in vacuo. The resulting residual oil was chromatographed on a column of silica gel with 30% ethyl acetate/hexanes as eluant to provide 6.06 g (48%) of product as a thick syrup that slowly crystallized upon standing. The structure of the product was confirmed as that of 1-(3-trifluoromethyl)phenyl-3-(3-chlorophenyl)-4-ethyl-2-pyrrolidone by IR, NMR and MS.

These and further compounds prepared by similar procedures are listed in Table I below, together with physical data in the form of refractive indices or melting points where such measurements were possible and physical descriptions where they were not.

TABLE I
COMPOUNDS

| No. | $R^1$ | $R^2$ | $R^3$ | $R^4$ | $n_D^{30}$ or m.p. °C. |
|---|---|---|---|---|---|
| 1 | 3-$CF_3$ | H | H | $CH_2Cl$ | waxy solid |
| 2 | 3-Cl-4-F | H | H | $CH_2Cl$ | waxy solid |
| 3 | 3-$CF_3$-4-F | H | H | $CH_2Cl$ | 1.5296 |
| 4 | 3-$CF_3$-6-F | H | H | $CH_2Cl$ | 101–102° C. |
| 5 | 3,6-di-F | H | H | $CH_2Cl$ | 1.5600 |
| 6 | 3-$CF_3$ | H | H | $CHClCH_3$ | thick syrup |
| 7 | 4-Cl | H | 3-Cl | $CH_2Cl$ | waxy solid |
| 8 | 3-$CF_3$ | H | 4-Cl | $CH_2Cl$ | waxy solid |
| 9 | 3-$CF_3$ | H | 4-F | $CH_2Cl$ | very thick syrup |
| 10 | 3-$CF_3$ | H | 4-$CH_3$ | $CH_2Cl$ | very thick syrup |
| 11 | 3-$CF_3$ | H | 3-Cl | $CH_2Cl$ | waxy solid |
| 12 | 3-$CF_3$ | H | 3-$CH_3$ | $CH_2Cl$ | thick syrup |
| 13 | 3-$CF_3$ | H | 3-F | $CH_2Cl$ | thick syrup |
| 14 | 3-$CF_3$ | H | 2,4-di-Cl | $CH_2Cl$ | thick syrup |
| 15 | 3-$CF_3$ | H | 2-Cl | $CH_2Cl$ | thick paste |
| 16 | 3-$CF_3$ | H | 3-$OCH_3$ | $CH_2Cl$ | thick syrup |
| 17 | 3-$CF_3$ | H | 3-$CF_3$ | $CH_2Cl$ | thick syrup |
| 18 | 3-$CF_3$ | H | 2-F | $CH_2CL$ | thick syrup |
| 19 | 3-$CF_3$ | H | 4-$CF_3$ | $CH_2Cl$ | 96.5–104 |
| 20 | 3-$CF_3$ | H | 3,5-di-Cl | $CH_2Cl$ | waxy solid |
| 21 | 3-$CF_3$ | H | 2,3,4,5,6-penta-F | $CH_2Cl$ | thick syrup |
| 22 | 3-$CF_3$ | H | 2,6-di-F | $CH_2Cl$ | thick syrup |
| 23 | 3-$CF_3$ | H | 2,4-di-F | $CH_2Cl$ | waxy solid |
| 24 | 3-$CF_3$ | H | 2,3-di-F | $CH_2Cl$ | thick syrup |
| 25 | 3-$CF_3$ | H | H | $C_2H_5$ | thick syrup |
| 26 | 3-$CF_3$ | H | 3,4-di-F | $CH_2Cl$ | thick syrup |
| 27 | 3-$CF_3$ | H | 3-Cl | $C_2H_5$ | 83–98 |
| 28 | 3-CN | H | 3-Cl | $C_2H_5$ | thick syrup |
| 29 | 3-$CF_3$ | Br | H | $C_2H_5$ | thick syrup |
| 30 | 3-Cl | H | 3-Cl | $C_2H_5$ | 76–84° C. |

The compounds listed in the foregoing table were tested for herbicidal activity by various methods and at various rates of application. The results of some of these tests are given below. As one skilled in the art is aware, the results obtained in herbicidal screening tests are affected by a number of factors that are not readily controllable. Environmental conditions such as amount of sunlight and water, soil type, soil pH, temperature and humidity, are examples of such factors. The depth of planting and the application rate of the herbicide, as well as the nature of crops being tested, can also affect the test results. Results will also vary from crop to crop and within the crop varieties.

The test procedures used are as follows:

Pre-Emergence Herbicidal Evaluation at 4 pounds/acre

Planting flats were filled with sandy loam soil containing a fungicide and fertilizer. The soil was leveled and rows of grassy weeds, broadleaf weeds and yellow nutsedge (*Cyperus esculentus*), were planted thickly enough so that several seedlings emerged per inch of row. The grassy weeds were yellow foxtail (*Setaria viridis*), watergrass (*Echinochloa crusgalli*) and wild oat (*Avena fatua*). Broadleaf weeds utilized were annual morningglory (*Ipomoea purpurea*), velvetleaf (*Abutilon theophrasti*), wild mustard (*Brassica kaber*), and curly dock (*Rumex crispus*).

Solutions of the test compounds were made by weighing out 333 mg of the test compound into a 60-mL wide-mouth bottle, then dissolving the compound in 25 mL of acetone containing 1% Tween ®20 (polyoxyethylene sorbitan monolaurate emulsifier). Additional solvents, not exceeding 5 mL. were used if needed to dissolve the compound. A 20.5-mL aliquot was then taken from the solution and diluted with 25 mL of an acetone:water mixture (19:1) containing 1% Tween200 20. This was used as the spray solution.

One day after planting, the flats were sprayed with the spray solution at a rate of 80 gallons of solution per acre with the compound being applied at a rate of 4 pounds per acre (4.48 kg/hectare).

The flats were then returned to the greenhouse and watered daily by sprinkling. The degree of weed control was estimated and recorded 3 weeks after treatment, as percentage control compared to the growth of the same species in an untreated check flat of the same age.

The percent control is the total injury to the plants due to all factors, including inhibited germination, killing of the plant tissue after emergence stunting. malformation, chlorosis, and other types of injury. The control ratings vary from 0 to 100 percent, where O represents no effect with growth equal to the untreated control, and 100 represents complete kill; a dash indicates that no test was performed at that level of application.

Post-Emergence Herbicidal Evaluation at 4 pounds/acre

The soil was prepared and seeded with the same varieties used in the pre-emergence test. The flats were placed in the greenhouse at 70-85° F. (21-29° C.) and watered by sprinkling. Twelve to fourteen days after planting, the flats were sprayed at a rate of 80 gallons of solution per acre. Each compound was applied at the rate of 4 pounds/ acre (4.48 kg/hectare). using a spray solution prepared as in the pre-emergence test.

The flats were returned to the greenhouse after spraying and watered daily without wetting the foliage, three weeks after treatment the degree of weed control was estimated and recorded as percentage control compared to the growth of the same species in an untreated check flat of the same age. The percent control ratings were assigned on the same basis as for the pre-emergence evaluation.

The following table lists the results of these tests, in terms of averages for the grasses and broadleaf weeds, with yellow nutsedge listed separately, in both pre-and post-emergence evaluations.

TABLE II

HERBICIDE TEST RESULTS
PERCENT CONTROL AT 4 LB/ACRE

| Compound | Pre-Emergence | | | Post-Emergence | | |
|---|---|---|---|---|---|---|
| No. | YNS | AVG | AVB | YNS | AVG | AVB |
| 1 | — | — | — | — | — | — |
| 2 | 0 | 13 | 33 | 0 | 0 | 28 |
| 3 | 0 | 80 | 54 | 0 | 67 | 54 |
| 4 | 0 | 0 | 0 | 0 | 13 | 36 |
| 5 | 0 | 10 | 0 | 0 | 0 | 35 |
| 6 | 0 | 0 | 0 | 0 | 0 | 38 |
| 7 | 0 | 0 | 0 | 0 | 0 | 0 |
| 8 | 0 | 12 | 13 | 0 | 10 | 38 |
| 9 | 0 | 99 | 70 | — | 73 | 49 |
| 10 | 0 | 0 | 0 | 0 | 0 | 41 |
| 11 | 0 | 96 | 70 | 0 | 45 | 60 |
| 12 | 0 | 87 | 65 | 0 | 55 | 76 |
| 13 | 0 | 90 | 90 | 25 | 68 | 73 |
| 14 | — | 0 | 4 | 0 | 0 | 3 |
| 15 | 0 | 8 | 15 | — | 0 | 29 |
| 16 | 0 | 57 | 18 | 0 | 10 | 49 |
| 17 | 0 | 60 | 68 | 0 | 33 | 78 |
| 18 | 0 | 0 | 0 | 0 | 0 | 0 |
| 19 | 0 | 0 | 0 | 0 | 0 | 9 |
| 20 | 0 | 58 | 43 | 0 | 18 | 38 |
| 21 | 0 | 25 | 18 | 0 | 18 | 69 |
| 22 | 0 | 0 | 3 | — | 8 | 23 |
| 23 | 0 | 53 | 23 | — | 25 | 53 |
| 24 | 0 | 65 | 40 | 0 | 100 | 95 |
| 25 | — | — | — | — | — | — |
| 26 | 0 | 93 | 100 | 0 | 80 | 70 |
| 27 | — | — | — | — | — | — |
| 28 | — | — | — | — | — | — |
| 29 | 0 | 93 | 83 | 0 | 63 | 60 |
| 30 | 0 | 93 | 92 | 0 | 50 | 85 |

Abbreviations:
YNS: Yellow Nutsedge
AVG: Grasses averaged
AVB: Broadleaf weeds averaged Herbical and Crop Injury Tets at 0.25–2.0 lb/acre Pre-emergence and post-emergence tests were performed at application rates ranging from 0.13 to 2.00 lb/acre (0.14 to 2.24 kg/hectare, based on the active ingredient) for a number of the compounds listed in Table I. This round of testing extended to both weed and crop species, and followed the same general procedure as the 4 lb/acre tests, except for the plant species used. The species were as follows:

| Grass weeds: | yellow foxtail | Setaria viridis |
| | annual ryegrass | Lolium multiflorum |
| | watergrass | Echinochloa crusgalli |
| | shattercane | Sorghum bicolor |
| | wild oat | Avena fatua |
| | broadleaf signalgrass | Brachiaria platyphylla |
| Broadleaf weeds: | annual morningglory | Ipomoea purpurea |
| | cocklebur | Xanthium pensylvanicum |
| | sesbania | Sesbania exasperata |
| | velvetleaf | Abutilon theophrasti |
| | sicklepod | Cassia obtusifloia |
| Other: | yellow nutsedge | Cyperus esculentus |
| Crops: | cotton | Gossypium herbaceum |
| | soybean | Glycine max |
| | corn | Zea mays |
| | milo | Sorghum vulgare |
| | wheat | Triticum aestivum |
| | rice | Oryza satvia |
| | sugarbeet | Beta vulgaris |

The results of these tests are listed in Table III, in which the indicia used are the same as those in Table II.

TABLE III

HERBICIDE AND CROP INJURY TEST RESULTS
PERCENT CONTROL AT 2 LB/ACRE AND LESS

| | Crops* | | | | | | | Weeds | | |
|---|---|---|---|---|---|---|---|---|---|---|
| Rate | (1) | (2) | (3) | (4) | (5) | (6) | (7) | YNS | AVG | AVB |
| Compound No. 25 - Pre-Emergence: | | | | | | | | | | |
| 0.25 | 0 | 75 | 35 | 75 | 40 | 10 | 100 | 0 | 63 | 37 |
| 0.50 | 0 | 35 | 40 | 70 | 30 | 10 | 100 | 0 | 83 | 52 |
| 1.00 | 0 | 50 | 75 | 100 | 40 | 20 | 100 | 0 | 98 | 73 |
| 2.00 | 10 | 60 | 75 | 100 | 50 | 35 | 100 | 0 | 100 | 93 |
| Compound No. 25 - Post-Emergence: | | | | | | | | | | |
| 0.25 | — | — | — | — | — | — | — | — | — | — |
| 0.50 | — | — | — | — | — | — | — | — | — | — |
| 1.00 | 50 | 75 | 60 | 60 | 30 | 40 | 100 | 0 | 99 | 82 |
| 2.00 | 45 | 75 | 65 | 65 | 30 | 25 | 100 | 0 | 96 | 86 |
| Compound No. 27 - Pre-Emergence: | | | | | | | | | | |
| 0.13 | 15 | 15 | 0 | 30 | 20 | 0 | 100 | 0 | 58 | 55 |
| 0.25 | 25 | 25 | 25 | 35 | 30 | 25 | 100 | 0 | 75 | 68 |
| 0.50 | 35 | 50 | 40 | 60 | 40 | 25 | 100 | 0 | 88 | 100 |
| 1.00 | 40 | 50 | 45 | 70 | 40 | 20 | 100 | 0 | 88 | 71 |
| 2.00 | 50 | 50 | 60 | 80 | 35 | 20 | 100 | 0 | 97 | 88 |
| Compound No. 27 - Post-Emergence: | | | | | | | | | | |
| 1.00 | 50 | 30 | 50 | 40 | 15 | 25 | 100 | 0 | 88 | 83 |
| 2.00 | 50 | 40 | 40 | 35 | 30 | 25 | 100 | 0 | 91 | 90 |
| Compound No. 28 - Pre-Emergence: | | | | | | | | | | |
| 0.25 | 25 | 25 | 35 | 30 | 0 | 0 | 100 | 0 | 58 | 52 |
| 0.50 | 20 | 40 | 40 | 35 | 10 | 25 | 100 | 0 | 75 | 65 |
| 1.00 | 30 | 50 | 50 | 80 | 10 | 15 | 100 | 20 | 83 | 80 |
| 2.00 | 40 | 60 | 65 | 80 | 25 | 20 | 100 | 0 | 86 | 99 |
| Compound No. 28 - Post-Emergence: | | | | | | | | | | |
| 0.25 | — | — | — | — | — | — | — | — | — | — |
| 0.50 | — | — | — | — | — | — | — | — | — | — |
| 1.00 | 40 | 40 | 50 | 40 | 0 | 0 | 100 | 15 | 76 | 96 |
| 2.00 | 40 | 50 | 50 | 40 | 40 | 15 | 100 | 35 | 96 | 99 |

*Crops:
(1) Cotton
(2) Soybean
(3) Corn
(4) Milo
(5) Wheat
(6) Rice
(7) Sugarbeet The compounds of the present invention are useful as herbicides and can be applied in a variety of ways known to those skilled in the art, at various concentrations. In practice, the compounds are applied as formulations containing the various adjuvants and carriers known to or used in the industry for facilitating dispersion. The choice of formulation and mode of application for any given compound may affect its activity, and selection will be made accordingly. The compounds of the invention may thus be formulated as granules, as wettable powders, as emulsifiable concentrates, as powders or dusts, as flowables, as solutions, suspensions or emulsions, or in controlled-release forms such as microcapsules. These formulations may contain as little as about 0.5% to as much as about 95% or more by weight of active ingredient. The optimum amount for any given compound will depend upon the nature of the seeds or plants to be controlled. The rate of application will generally vary from about 0.01 to about 10 pounds per acre. preferably from about 0.02 to about 4 pounds per acre.

Wettable powders are finely divided particles which disperse readily in water or other liquid carriers. The particles contain the active ingredient retained in a solid matrix. Typical solid matrices include fuller3's earth. kaolin clays, silicas and other readily wet organic or inorganic solids. Wettable powders normally contain about 5% to about 95% of the active ingredient plus a small amount of wetting, dispersing, or emulsifying agent.

Emulsifiable concentrates are homogeneous liquid compositions dispersible in water or other liquid, and may consist entirely of the active compound with a liquid or solid emulsifying agent, or may also contain a liquid carrier, such as xylene, heavy aromatic naphthas, isophorone and other non-volatile organic solvents. In use, these concentrates are dispersed in water or other liquid and normally applied as a spray to the area to be treated. The amount of active ingredient may range from about 0.5% to about 95% of the concentrate.

Granular formulations include both extrudates and relatively coarse particles, and are usually applied without dilution to the area in which suppression of vegetation is desired. Typical carriers for granular formulations include sand, fuller's earth, attapulgite clay, bentonite clays, montmorillonite clay, vermiculite, perlite and other organic or inorganic materials which absorb or which can be coated with the active compound. Granular formulations normally contain about 5% to about 25% active ingredients which may include surface-active agents such as heavy aromatic naphthas, kerosene or other petroleum fractions, or vegetable oils: and/or stickers such as dextrins, glue or synthetic resins.

Dusts are free-flowing admixtures of the active ingredient with finely divided solids such as talc, clays, flours and other organic and inorganic solids which act as dispersants and carriers.

Microcapsules are typically droplets or granules of the active material enclosed in an inert porous shell which allows escape of the enclosed material to the surroundings at controlled rates. Encapsulated droplets are typically about 1 to 50 microns in diameter. The enclosed liquid typically constitutes about 50 to 95% of the weight of the capsule, and may include solvent in addition to the active compound. Encapsulated granules are generally porous granules with porous membranes sealing the granule pore openings, retaining the active species in liquid form inside the granule pores. Granules typically range from 1 millimeter to 1 centimeter, preferably 1 to 2 millimeters in diameter. Granules are formed by extrusion, agglomeration or prilling, or are naturally occurring. Examples of such materials are vermiculite, sintered clay, kaolin, attapulgite clay, sawdust and granular carbon. Shell or membrane materials include natural and synthetic rubbers, cellulosic materials, styrene-butadiene copolymers, polyacrylonitriles, polyacrylates, polyesters, polyamides, polyureas, polyurethanes and starch xanthates.

Other useful formulations for herbicidal applications include simple solutions of the active ingredient in a solvent in which it is completely soluble at the desired concentration, such as acetone, alkylated napthalenes, xylene and other organic solvents. Pressurized sprays, wherein the active ingredient is dispersed in finely-divided form as a result of vaporization of a low boiling dispersant solvent carrier, such as the Freons, may also be used.

Many of these formulations include wetting, dispersing or emulsifying agents. Examples are alkyl and alkylaryl sulfonates and sulfates and their salts; polyhydric alcohols: polyethoxylated alcohols: esters and fatty amines. These agents when used normally comprise from 0.1% to 15% by weight of the formulation.

The compounds of the present invention are also useful when combined with other herbicides and/or defoliants, dessicants, growth inhibitors, and the like. These other materials can comprise from about 5% to about 95% of the active ingredients in the formulations. These combinations frequently provide a higher level of effectiveness in controlling weeds and often provide results unattainable with separate formulations of the individual herbicides.

Examples of other herbicides, defoliants, dessicants and plant growth inhibitors with which the compounds of this invention can be combined are:

chlorophenoxy herbicides such as 2,4-D, 2,4,5-T, MCPA, MCPB, 2,4-DB, 2,4-DEB, 4-CPA, 2,4,5-TB, and silvex;

carbamate herbicides such as propham, chlorpropham, swep, and barban:

thiocarbamate and dithiocarbamate herbicides such as CDEC, metham-sodium, EPTC, diallate, PEBC, and vernolate;

substituted urea herbicides such as norea, dichloral urea, chloroxuron, cycluron, fenuron, monuron, monuron TCA, diuron, linuron, monolinuron neburon, buturon and trimeturon:

symmetrical triazine herbicides such as simazine chlorazine desmetryne, norazine, ipazine, prometryn, atrazine, trietazine, simetone, prometone, propazine and ametryne:

chlorinated aliphatic acid herbicides such as TCA and dalapon;

chlorinated benzoic acid and phenylacetic acid herbicides such as 2.3,6-TBA, dicamba, tricamba, chloramben, fenac, PBA, 2-methoxy-3.6-dichlorophenylacetic acid, 3-methoxy-2.6-dichlorophenylacetic acid 2-methoxy-3 5.6-trichlorophenylacetic acid and 2.4-dichloro-3-nitrobenzoic acid:

and such compounds as aminotriazole, maleic hydrazide, phenylmercury acetate, endothal, technical chlordane, DCPA, diquat, erbon, DNC, DNBP, dichlobenil, DPA, diphenamide, dipropalin, trifluralin, solan, dicryl, merphos, DMPA, DSMA, MSMA, potassium azide, acrolein, benefin, bensulide, AMS, bromacil, 2-(3,4-dichlorophenyl)-4-methyl-1,2,4-oxazolidine-3,5-dione, bromoxynil, cacodylic acid, CMA, CPMF, cypromid, DCB, DCPA, dichlone, diphenatril, DMTT, DNAP, EBEP, EXD, HCA, ioxynil, IPX, isocil, potassium cyanate, MAA, MAMA, MCPES, MCPP, MH, molinate, NPA, OCH, paraquat, PCP, picloram, DPA, PCA, sesone, terbacil, terbutol, TCBA, alachlor, nitralin, sodium tetraborate, calcium cyanamide, S,S,S-tributylphosphorotrithioate and propanil.

These formulations can be applied to the areas where control is desired by conventional methods. Dust and liquid compositions, for example, can be applied by the use of power-dusters boom and hand sprayers and spray dusters, The formulations can also be applied from airplanes as a dust or a spray or by rope wick applications. To modify or control growth of germinating seeds or emerging seedlings, dust and liquid formulations can be distributed in the soil to a depth of at least one-half inch below the soil surface or applied to the soil surface only, by spraying or sprinkling. The formulations can also be applied by addition to irrigation water. This permits penetration of the formulations into the soil together with the irrigation water. Dust compositions, granular compositions or liquid formulations applied to the surface of the soil can be distributed below the surface of the soil by conventional means such as discing, dragging or mixing operations.

The following are examples of typical formulations.

| 5% dust: | 5 parts active compound |
| | 95 parts talc |
| 2% dust: | 2 parts active compound |
| | 1 part highly dispersed silicic acid |
| | 97 parts talc |

These dusts are formed by mixing the components then grinding the mixture to the desired particle size.

| 5% granules: |
| --- |
| 5 parts active compound |
| 0.25 part epichlorohydrin |
| 0.25 part cetyl polyglycol ether |
| 3.5 parts polyethylene glycol |
| 91 parts kaolin (particle size 0.3–0.8 mm) |

Granules are formed by mixing the active compound with epichlorohydrin and dissolving the mixture in 6 parts of acetone. The polyethylene glycol and cetyl polyglycol ether are then added. The resultant solution is sprayed on the kaolin and the acetone evaporated in vacuo.

| | wettable powders: |
| --- | --- |
| 70%: | 70 parts active compound |
| | 5 parts sodium dibutylnaphthylsulfonate |
| | 3 parts naphthalenesulfonic acid/phenolsulfonic acid/formaldehyde condensate (3:2:1) |
| | 10 parts kaolin |
| | 12 parts Champagne chalk |
| 40%: | 40 parts active compound |
| | 5 parts sodium lignin sulfonate |
| | 1 part sodium dibutylnaphthalenesulfonic acid |
| | 54 parts silicic acid |
| 25%: | 25 parts active compound |
| | 4.5 parts calcium lignin sulfate |
| | 1.9 parts Champagne chalk/hydroxyethyl cellulose (1:1) |
| | 1.5 parts sodium dibutylnaphthalenesulfonate |
| | 19.5 parts silicic acid |
| | 19.5 parts Champagne chalk |
| | 28.1 parts kaolin |
| 25%: | 25 parts active compound |
| | 2.5 parts isooctylphenoxy-polyethylene-ethanol |
| | 1.7 parts Champagne chalk/hydroxyethyl cellulose (1:1) |
| | 8.3 parts sodium aluminum silicate |
| | 16.5 parts kieselguhr |
| | 46 parts kaolin |
| 10%: | 10 parts active compound |
| | 3 parts of a mixture of sodium salts of saturated fatty alcohol sulfates |
| | 5 parts naphthalenesulfonic acid/formaldehyde condensate |
| | 82 parts kaolin |

These wettable powders are prepared by intimately mixing the active compounds with the additives in suitable mixers, and grinding the resulting mixtures in mills or rollers.

| 25% emulsifiable concentrate: |
| --- |
| 25 parts active substance |
| 2.5 parts epoxidized vegetable oil |
| 10 parts of an alkylarylsulfonate/fatty alcohol polyglycol ether mixture |
| 5 parts dimethylformamide |
| 57.5 parts xylene |

What is claimed is:

1. A compound having the formula

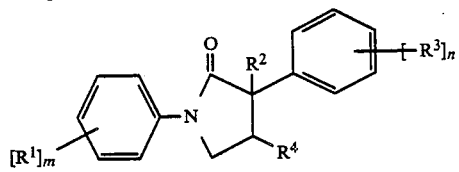

in which:
m is 1, 2, 3, 4 or 5;
n is 0, 1, 2, 3, 4 or 5;
$R^1$ is a member selected from the group consisting of halogen, trifluoromethyl, cyano, $C_1$–$C_4$ alkyl and $C_1$–$C_4$ alkoxy, and, when m is greater than 1, may be either a single such member or a combination thereof;
$R^2$ is a member selected from the group consisting of H and halogen;
$R^3$ is a member selected from the group consisting of halogen, trifluoromethyl, cyano, $C_1$–$C_4$ alkyl and $C_1$–$C_4$ alkoxy, and, when n is greater than 1, may be either a single such member or a combination thereof; and
$R^4$ is a member selected from the group consisting of $C_1$–$C_4$ alkyl and halogen-substituted $C_1$–$C_4$ alkyl.

2. A compound according to claim 1 in which $R^1$ is a member selected from the group consisting of halogen, trifluoromethyl and cyano.

3. A compound according to claim 1 in which $R^1$ is a member selected from the group consisting of halogen and trifluoromethyl.

4. A compound according to claim 1 in which $R^1$ is a member selected from the group consisting of chloro, fluoro and trifluoromethyl.

5. A compound according to claim 1 in which m is 1 or 2.

6. A compound according to claim 1 in which m is 1 or 2 and $R^1$ occupies the meta- or para-position.

7. A compound according to claim 1 in which m is 1 and $R^1$ occupies the meta-position.

8. A compound according to claim 1 in which m is 1 and $R^1$ is meta-trifluoromethyl.

9. A compound according to claim 1 in which $R^2$ is H.

10. A compound according to claim 1 in which $R^3$ is a member selected from the group consisting of halogen, $C_1$–$C_4$ alkyl and $C_1$–$C_4$ alkoxy.

11. A compound according to claim 1 in which $R^3$ is a member selected from the group consisting of halogen, $C_2$–$C_2$ alkyl and $C_1$–$C_2$ alkoxy.

12. A compound according to claim 1 in which $R^3$ is a member selected from the group consisting of chloro, fluoro, $C_1$–$C_2$ alkyl and $C_1$–$C_2$ alkoxy.

13. A compound according to claim 1 in which $R^3$ is a member selected from the group consisting of chloro, fluoro, methyl and methoxy.

14. A compound according to claim 1 in which n is 0, 1 or 2.

15. A compound according to claim 1 in which n is 1 or 2.

16. A compound according to claim 1 in which n is 1 and $R^3$ occupies the meta-position.

17. A compound according to claim 1 in which n is 1 and $R^3$ is F.

18. A compound according to claim 1 in which n is 1 and $R^3$ is meta-F.

19. A compound according to claim 1 in which $R^4$ is a member selected from the group consisting of methyl, ethyl, halomethyl and haloethyl.

20. A compound according to claim 1 in which $R^4$ is a member selected from the group consisting of halomethyl and ethyl.

21. A compound according to claim 1 in which $R^4$ is a member selected from the group consisting of chloromethyl and ethyl.

22. A compound according to claim 1 in which $R^4$ is ethyl.

23. A compound according to claim 1 in which m is 1, n is 1, $R^1$ is meta-trifluoromethyl, $R^2$ is H, $R^3$ is meta-chloro. and $R^4$ is $CH_2Cl$.

24. A compound according to claim 1 in which m is 1, n is 1, $R^1$ is meta-trifluoromethyl, $R^2$ is H, $R^3$ is meta-fluoro and $R^4$ is $CH_2Cl$.

25. A compound according to claim 1 in which m is 1 n is 1, $R^1$ is meta-trifluoromethyl, $R^2$ is H, $R^3$ is meta-trifluoromethyl, and $R^4$ is $CH_2Cl$.

26. A compound according to claim 1 in which m is 1, n is 2, $R^1$ is meta-trifluoromethyl, $R^2$ is H, and $R^3$ is 3,4-difluoro, and $R^4$ is $CH_2Cl$.

27. An herbicidal composition comprising:
(a) an herbicidally effective amount of a compound having the formula

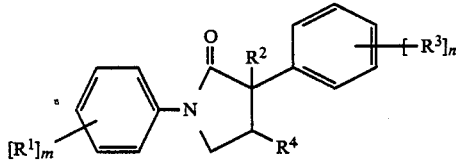

in which:
m is 1, 2, 3, 4 or 5;
n is 0, 1, 2, 3, 4 or 5;
$R^1$ is a member selected from the group consisting of halogen, trifluoromethyl, cyano, $C_1-C_4$ alkyl and $C_1-C_4$ alkoxy, and, when m is greater than 1, may be either a single such member or a combination thereof:
$R^2$ is a member selected from the group consisting of H and halogen:
$R^3$ is a member selected from the group consisting of halogen, trifluoromethyl, cyano, $C_1-C_4$ alkyl and $C_1-C_4$ alkoxy, and, when n is greater than 1, may be either a single such member or a combination thereof: and
$R^4$ is a member selected from the group consisting of $C_1-C_4$ alkyl and halogen-substituted $C_1-C_4$ alkyl:
(b) an herbicidally suitable inert diluent or carrier.

28. An herbicidal composition according to claim 27 in which $R^1$ is a member selected from the group consisting of halogen, trifluoromethyl and cyano.

29. An herbicidal composition according to claim 27 in which $R^1$ is a member selected from the group consisting of halogen and trifluoromethyl.

30. An herbicidal composition according to claim 27 in which $R^1$ is a member selected from the group consisting of chloro, fluoro and trifluoromethyl.

31. An herbicidal composition according to claim 27 in which m is 1 or 2.

32. An herbicidal composition according to claim 27 in which m is 1 or 2 and $R^1$ occupies the meta- or para-position.

33. An herbicidal composition according to claim 27 in which m is 1 and $R^1$ occupies the meta-position.

34. An herbicidal composition according to claim 27 in which m is 1 and $R^1$ is meta-trifluoromethyl.

35. An herbicidal composition according to claim 27 in which $R^2$ is H.

36. An herbicidal composition according to claim 27 in which $R^3$ is a member selected from the group consisting of halogen, $C_1-C_4$ alkyl and $C_1-C_4$ alkoxy.

37. An herbicidal composition according to claim 27 in which $R^3$ is a member selected from the group consisting of halogen, $C_1-C_2$ alkyl and $C_1-C_2$ alkoxy.

38. An herbicidal composition according to claim 27 in which $R^3$ is a member selected from the group consisting of chloro, fluoro, $C_1-C_2$ alkyl and $C_1-C_2$ alkoxy.

39. An herbicidal composition according to claim 27 in which $R^{39}$ is a member selected from the group consisting of chloro, fluoro, methyl and methoxy.

40. An herbicidal composition according to claim 27 in which n is 0, 1 or 2.

41. An herbicidal composition according to claim 27 in which n is 1 or 2.

42. An herbicidal composition according to claim 27 in which n is 1 and $R^3$ occupies the meta-position.

43. An herbicidal composition according to claim 27 in which n is 1 and $R^3$ is F.

44. An herbicidal composition according to claim 27 in which n is 1 and $R^3$ is meta-F.

45. An herbicidal composition according to claim 27 in which $R^4$ is a member selected from the group consisting of methyl, ethyl, halomethyl and haloethyl.

46. An herbicidal composition according to claim 27 in which $R^4$ is a member selected from the group consisting of halomethyl and ethyl.

47. An herbicidal composition according to claim 27 in which $R^4$ is a member selected from the group consisting of chloromethyl and ethyl.

48. An herbicidal composition according to claim 27 in which $R^4$ is ethyl.

49. An herbicidal composition according to claim 27 in which m is 1, n is 1, $R^1$ is meta-trifluoromethyl, $R^2$ is H, $R^3$ is meta-chloro, and R, is $CH_2Cl$.

50. An herbicidal composition according to claim 27 in which m is 1, n is 1, $R^1$ is meta-trifluoromethyl, $R^2$ is H, $R^3$ is meta-fluoro, and $R^4$ is $CH_2Cl$.

51. An herbicidal composition according to claim 27 in which m is 1, n is 1, $R^1$ is meta-trifluoromethyl, $R^2$ is H, $R^3$ is meta-trifluoromethyl, and $R^4$ is $CH_2Cl$.

52. An herbicidal composition according to claim 27 in which m is 1, n is 2, $R^1$ is meta-trifluoromethyl, $R^2$ is H, and $R^3$ is 3.4-difluoro, and $R^4$ is $CH_2Cl$.

53. A method of controlling undesirable vegetation comprising applying to said vegetation or to the locus thereof an herbicidally effective amount of a compound having the formula

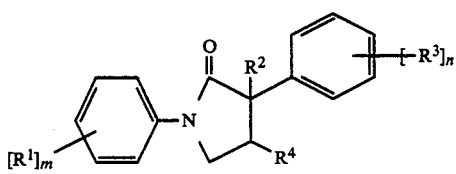

in which:
m is 1, 2, 3, 4 or 5;
n is 0, 1, 2, 3, 4 or 5;
$R^1$ is a member selected from the group consisting of halogen, trifluoromethyl, cyano $C_1$-$C_4$ alkyl and $C_1$-$C_4$ alkoxy, and, when m is greater than 1, may be either a single such member or a combination thereof:
$R^2$ is a member selected from the group consisting of H and halogen:
$R^3$ is a member selected from the group consisting of halogen, trifluoromethyl, cyano, $C_1$-$C_4$ alkyl and $C_1$-$C_4$ alkoxy, and, when n is greater than 1, may be either a single such member or a combination thereof; and
$R^4$ is a member selected from the group consisting of $C_1$-$C_4$ alkyl and halogen-substituted $C_1$-$C_4$ alkyl.

54. A method according to claim 53 in which $R^1$ is a member selected from the group consisting of halogen, trifluoromethyl and cyano.

55. A method according to claim 53 in which $R^1$ is a member selected from the group consisting of halogen and trifluoromethyl.

56. A method according to claim 53 in which $R^1$ is a member selected from the group consisting of chloro, fluoro and trifluoromethyl.

57. A method according to claim 53 in which m is 1 or 2.

58. A method according to claim 53 in which m is 1 or 2 and $R^1$ occupies the meta- or para-position.

59. A method according to claim 53 in which m is 1 and $R^1$ occupies the meta-position.

60. A method according to claim 53 in which m is 1 and $R^1$ is meta-trifluoromethyl.

61. A method according to claim 53 in which $R^2$ is H,

62. A method according to claim 53 in which $R^3$ is a member selected from the group consisting of halogen, $C_1$-$C_4$ alkyl and $C_1$-$C_4$ alkoxy.

63. A method according to claim 53 in which $R^3$ is a member selected from the group consisting of halogen $C_1$-$C_2$ alkyl and $C_1$-$C_2$ alkoxy.

64. A method according to claim 53 in which $R^3$ is a member selected from the group consisting of chloro, fluoro, $C_1$-$C_2$ alkyl and $C_1$-$C_2$ alkoxy.

65. A method according to claim 53 in which $R^3$ is a member selected from the group consisting of chloro, fluoro, methyl and methoxy.

66. A method according to claim 53 in which n is 0, 1 or 2.

67. A method according to claim 53 in which n is 1 or 2.

68. A method according to claim 53 in which n is 1 and $R^3$ occupies the meta-position.

69. A method according to claim 53 in which n is 1 and $R^3$ is F.

70. A method according to claim 53 in which n is 1 and $R^3$ is meta-F.

71. A method according to claim 53 in which $R^4$ is a member selected from the group consisting of methyl, ethyl, halomethyl and haloethyl.

72. A method according to claim 53 in which $R^4$ is a member selected from the group consisting of halomethyl and ethyl.

73. A method according to claim 53 in which $R^4$ is a member selected from the group consisting of chloromethyl and ethyl.

74. A method according to claim 53 in which $R^4$ is ethyl.

75. A method according to claim 53 in which m is 1, n is 1. $R^1$ is meta-trifluoromethyl, $R^2$ is H, $R^3$ is meta-chloro, and $R^4$ is $CH_2Cl$.

76. A method according to claim 53 in which m is 1, n is 1 $R^1$ is meta-trifluoromethyl, $R^2$ is H, $R^3$ is meta-fluoro and $R^4$ is $CH_2Cl$.

77. A method according to claim 53 in which m is 1 n is 1 $R^1$ is meta-trifluoromethyl, $R^2$ is H, $R^3$ metatrifluoromethyl, and $R^4$ is $CH_2Cl$.

78. A method according to claim 53 in which m is 1, n is 2. $R^1$ is meta-trifluoromethyl, $R^2$ is H, and $R^3$ 3,4-difluoro and $R^4$ is $CH_2Cl$.

* * * * *

UNITED STATES PATENT AND TRADEMARK OFFICE
CERTIFICATE OF CORRECTION

PATENT NO. : 4,960,457
DATED : October 2, 1990
INVENTOR(S) : Frank X. Woolard

It is certified that error appears in the above-identified patent and that said Letters Patent is hereby corrected as shown below:

In Column 16, line 31, "$R^{39}$" should read --- $R^3$ ---.

In Column 16, line 56, "R" should read --- $R^4$ ---.

Signed and Sealed this

Eighth Day of February, 1994

*Attest:*

BRUCE LEHMAN

*Attesting Officer*  *Commissioner of Patents and Trademarks*